United States Patent [19]

Mitsch

[11] 4,446,068

[45] May 1, 1984

[54] N-SUBSTITUTED FLUOROAZIRIDINES AND PROCESS FOR MAKING

[75] Inventor: Ronald A. Mitsch, St. Paul, Minn.

[73] Assignee: The United States of America as represented by the Secretary of the Navy, Washington, D.C.

[21] Appl. No.: 628,313

[22] Filed: Apr. 4, 1967

[51] Int. Cl.$^3$ .......................................... C07D 203/22
[52] U.S. Cl. .................................... 260/239 E; 8/191; 260/239 AA; 526/315; 528/429; 528/425; 564/249; 570/134; 570/141
[58] Field of Search .................................... 260/239 E

[56] References Cited

U.S. PATENT DOCUMENTS 3,070,596 12/1962 Graefe et al. ........................ 260/239
3,328,391 6/1967 Sandri et al. ........................ 260/239

OTHER PUBLICATIONS

Hine, "Divalent Carbon", (Ronald Press Co., New York, 1964), p. 7.

Primary Examiner—Alton D. Rollins
Attorney, Agent, or Firm—Robert F. Beers; Kenneth E. Walden; Roger D. Johnson

[57] ABSTRACT

N-substituted fluoroaziridines useful as chemical intermediates and process for making by reaction of fluoroazines with fluorocarbenes.

1 Claim, No Drawings

N-SUBSTITUTED FLUOROAZIRIDINES AND PROCESS FOR MAKING

BACKGROUND

Although hydrocarbon aziridines are known which contain functional substituents on the nitrogen atom of the ring, there are no perfluoroaziridines reported in the chemical literature. In particular, there are no fluoroaziridines which have a functional substituent at the nitrogen atom of the aziridine ring. It has been found that, whereas hydrocarbon aziridines are quite susceptible to nucleophilic ring opening reactions, the fluoroaziridine analogues are, on the contrary, surprisingly resistant to nucleophilic ring opening reactions. As a consequence of the improved stability of the fluoroaziridine ring, the chemical reactions of the functional substituents of fluoroaziridines, such as hydrolysis, can be carried out without appreciable decomposition of the fluoroaziridine ring.

SUMMARY

One process and some products of this invention are illustrated by the following generalized equation:

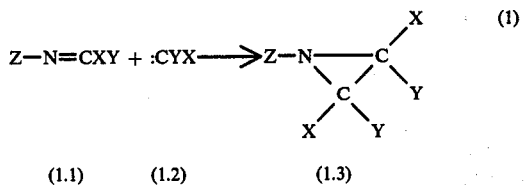

where X and Y are each selected from the group consisting of fluorine, chlorine, bromine, difluoroamino, cyano, isocyanato, alkoxy radicals, and fluoroaliphatic radicals; Z is selected from the group consisting of

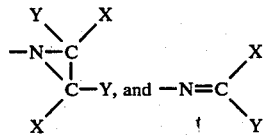

A fluoroaliphatic radical for purposes of this invention is a fluorinated aliphatic radical containing at least one carbon atom in the skeletal chain. The chain may be straight, branched, or cyclic, and may be interrupted by divalent oxygen atoms, divalent sulphur atoms, trivalent nitrogen atoms, the divalent radical $=SF_4$, or the divalent radical $=SO_2$. Preferably the fluoroaliphatic radical contains no functional groups. Preferably, such skeletal chain does not contain more than one hetero atom for every two carbon atoms in the skeletal chain. It is preferred to have only fluorine present as substituents to satisfy non-skeletal valences. An occasional hydrogen atom, bromine atom or chlorine atom may be present as substituents in such fluoroaliphatic radicals preferably not more than one such non-fluorine substituent being present in such radical for every two carbon atoms.

Preferably, an alkoxy radical or a fluoroaliphatic radical contains less than about 20 carbon atoms in its skeletal chain. Lower alkoxy radicals and lower fluoroaliphatic radicals are more preferred. The term "lower" as used in this invention in describing a radical has reference to a radical containing less than 7 carbon atoms.

As illustrated by generalized equation (1), the compounds of the invention are conveniently prepared by the reaction of a fluorocarbene of formula (1.2) with a fluoroazine of formula (1.1). Fluorocarbenes are known reactive intermediates, see, for example, "Carbene Chemistry", W. Kirmse, Academic Press, New York (1964) and "Divalent Carbon", J. Hine, Ronald Press Company, New York (1964). One useful group of fluorocarbenes with formula (1.2) is that derived from certain novel diazirines of the formula

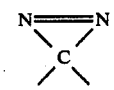

wherein the free valences are satisfied by covalently bonded fluorine and other substituents.

Examples of other substituents include alkoxy, chlorine, cyano, difluoramino, bromine, fluoroaliphatic and isocyanato. Diazirines of this type are disclosed in applicant's U.S. patent application Ser. No. 307,730, now U.S. Pat. No. 3,637,663.

Other methods for the production of carbenes are known, e.g., the pyrolysis of salts of perhaloacetic acids, pyrolysis and/or photolysis of diazo compounds, such as $(CF_3)_2CN_2$, $CH_2N_2$, $CF_3(CN)CN_2$, and the like. However, these carbene generation techniques are generally less preferred than the use of diazirines as carbene precursors.

The fluoroazines of formula (1.1) are well known to the art. Methods of preparation for these fluoroazines can be found in U.S. Pat. No. 3,117,996, as well as in non-patent literature.

Fluoroazines of formula (1.1) include those claimed in U.S. Pat. No. 3,117,996 which are of the general formula R—CF=N—N=CF—R, where R is selected from the group consisting of perfluoroalkyl radicals of from 2 to 12 carbons and ω-hydroperfluoroalkyl radicals of 2 to 12 carbons. In addition, fluoroazines of formula (1.1) are conveniently prepared by pyrolysis of fluorodiazirines.

The compounds of formula (1.3) are novel products of this invention and are termed herein (N-substituted)-fluoroaziridines. Preferred compounds of formula (1.3) prepared by the reaction of a fluorocarbene of formula (1.2) with a fluoroazine of formula (1.1) are shown in the following Table I:

TABLE I

| Fluoroazine of formula (1.1) | Fluorocarbene of formula (1.2) | (N—Substituted)fluoro- aziridine of formula (1.3) |
|---|---|---|
| $CF_2=N—N=CF_2$ | $CF_3CF:$ | $CF_2=N—N — CF_2CFCF_3$ |
| $ClCF=N—N=CFCl$ | $NF_2CF:$ | $ClCF=N—N—CFClCFNF_2$ |

TABLE I-continued

| Fluoroazine of formula (1.1) | Fluorocarbene of formula (1.2) | (N—Substituted)fluoro-aziridine of formula (1.3) |
| --- | --- | --- |
| NCCF=N—N=CFCN | C₄H₉OCF: | NCCF=N—N—$\overline{\text{CF(CN)CFOC}_4\text{H}_9}$ + |
|  |  | $[—\overline{\text{NCF(CN)CFOC}_4\text{H}_9}]_2$ |
| C₅F₁₁CF=N—N=CFC₅F₁₁ | BrCF: | C₅F₁₁CF=N—$\overline{\text{NCF(C}_5\text{F}_{11}\text{)CFBr}}$ |
| (CF₃)₂C=N—N=C(CF₃)₂ | O=C=NCF: | (CF₃)₂C=N—N—$\overline{\text{C(CF}_3)_2\text{CFNCO}}$ + |
|  |  | $[—\overline{\text{N—C(CF}_3)_2\text{CFNCO}}]_2$ |
| $\overline{\text{CF}_2\text{CF(C}_{12}\text{F}_{24}\text{H)—N}}$ (HF₂₄C₁₂)CF=N | CH₃OCF: | $\overline{\text{CF}_2\text{CF(C}_{12}\text{F}_{24}\text{H)—N}}$ CH₃OCFCF(C₁₂H₂₄)—N |
| CFBr=N—N=CFBr | BrCF: | CFBr=N—$\overline{\text{NCFBrCFBr}}$ + |
|  |  | $\overline{\text{CFBrCFBrN}}$—$\overline{\text{NCFBrCFBr}}$ |
| CF₂=N—N=CF₂ | CF₃CH₂OCF: | CF₂=N—$\overline{\text{NCF}_2\text{CFOCH}_2\text{CF}_3}$ |

In reacting a fluoroazine of formula (1.1) with a fluorocarbene of formula (1.2) in accordance with equation (1) above, one can employ liquid or vapor phase conditions in which such fluoroazine is contacted with such fluorocarbene while maintaining a temperature ranging from about −50° C. to 125° C. The optimum time, temperature and pressure (e.g. vapor phase) conditions for a given reaction vary widely depending on such variables as the reactivity of the fluorocarbene and the fluoroazine, respectively, the quantity of the reagents utilized, the dilution of reagents, and the like.

Typically, and conveniently, the fluoroazine is prepared separately from and prior to the time when the fluoroaziridine-forming reaction is carried out. Owing to its reactive character it is much preferred to generate the fluorocarbene concurrently with or in the presence of the fluoroazine, as taught herein.

In general, by the preferred process conditions of this invention, a fluorocarbene precursor and a fluoroazine are first mixed. The mixing can be accomplished either under gas phase conditions (preferred) or in liquid phase conditions. If in liquid phase conditions, it is preferred to employ an inert (e.g. free from Zerewitinoff active hydrogen) organic liquid diluent which is a solvent both for the fluoroazine and for the fluorocarbene.

The inert organic liquid diluent chosen in any given situation depends upon such matters as the properties of the fluoroazine and the fluorocarbene being used, and the conditions of the reaction. Thus, under the particular process conditions being used, the diluent must be liquid, capable of dissolving a sufficient amount of each respective class of reactant to permit the reaction to proceed at a practical rate, and inert with respect to the materials present. Among the suitable organic liquid diluents are dichloromethane, chloroform, carbon tetrachloride, benzene, toluene, chlorobenzene, acetonitrile, chlorotrifluoromethane, etc. The diluent is chosen so as to have a boiling point which will facilitate its separation from reaction products by distillation, vapor phase chromatography, liquid chromatography, evaporation, etc.

In general, a mixture of fluorocarbene precursor and excess fluoroazine, in accordance with this invention, is subjected either to photolysis conditions, or to pyrolysis conditions, or to both conditions. The fluorocarbene need not be isolated (although this reactive intermediate can be identified if desired), but is preferably allowed to remain in a reaction mixture and reacts with the fluoroazine present, leading to the formation of fluoroaziridines of formula (1.3).

Typical photolysis conditions involve the use of ultraviolet light (wavelengths of from about 3000 to 4000 Å units) and temperatures ranging from about −50° C. to 125° C.

Typical pyrolysis conditions involve the use of temperatures ranging from about +50° to 125° C. The conditions of the reaction, either pyrolysis, photolysis, or both, are determined by the reactivity of the fluoroazine and fluorocarbene employed. For fluoroazines and fluorocarbenes of low reactivity, e.g., those substituted by perfluoroalkyl groups, higher temperatures are required. In general, pyrolysis is generally the preferred fluoroaziridine generation technique if the fluorocarbene intermediate tends to undergo intramolecular isomerization, for example, NF$_2$CF: isomerizes readily to CF$_2$=NF.

Temperatures above about 125° C. are undesirable in most cases because the fluoroaziridine ring may undergo a reverse reaction involving the elimination of the carbene which has been added. The reaction time should be of sufficient length to permit the reaction to be completed. If the fluorodiazirines or carbene precursors employed are generally gases, it is convenient to monitor the extent of completion of the reaction by infrared spectral examination of the volatile components of the mixture. In this way the extent of completion of a reaction can be followed by observing when the characteristic absorption peak(s) of the diazirine ring or other carbene precursor either disappears or is greatly weakened, so that the process can be terminated at an appropriate time.

The reaction mixtures are separated according to the physical properties of the products obtained; for example, by gas liquid chromatography if the products are gases at ordinary temperature, or by usual fractional distillation techniques when the products are liquids.

Functional substituents (such as —NF$_2$, —OCH$_3$, —CN, —NCO, etc.) which are on the fluoroaziridine ring can be produced into the compounds of formula (1.3) as part of the starting fluoroazine or the starting fluorocarbene. It will be appreciated by those skilled in the art that both starting materials of formula (1.3) can contain one or more functional substituents. In general, a substituent or moiety which is bonded to the nitrogen atom of a fluoroaziridine ring can be considered to be functional in this invention if it contains or comprises an amino (—NH$_2$ or —NH—) group or an amino (—N=CXY) group.

Certain of the fluoroaziridines of formula (1.3) containing imino groups bonded directly to the fluoroaziridine ring nitrogen atom can be hydrolyzed with water to the corresponding fluorinated primary amines and fluorinated isocyanates and thus these fluoroaziridines are useful intermediates for the preparation of other novel fluoroaziridines of the present invention, as illustrated by the following generalized equation:

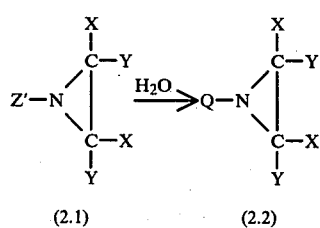

where X and Y are as defined above, Z' is selected from the group consisting of

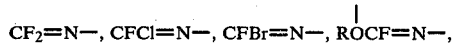

R' is an alkyl radical of preferably from 1 through 20 carbon atoms, and Q is selected from the group consisting of

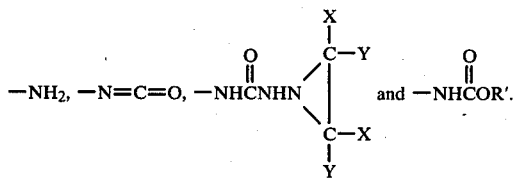

More preferably, R' in formula (2.2) compounds is a lower alkyl radical.

The controlled hydrolysis of the starting compounds of formula (2.1) in accordance with the present invention, is carried out by maintaining such compounds in contact with stoichiometric or excess amounts of water for a length of time which is sufficient to convert substantially all of the imino groups thereof to fluoroaziridines of formula (2.2).

Although such hydrolyses can be carried out in basic environment, that is, an environment wherein the pH is greater than 7, (i.e. which is not strongly basic), the yield of fluoroaziridine product of formula (2.2) is reduced in such instances, presumably due to decomposition, as, for example, by further hydrolysis of products. Therefore, a pH of about 7 or below is preferred in practicing the hydrolysis teachings of this invention. While the hydrolysis reaction can be carried out with the fluoroaziridine starting material present primarily in the gas phase, it is more preferred to use an organic mutual solvent in which both water and starting fluoroaziridine of formula (2.1) are soluble. Such mutual solvent should be inert towards the fluoroaziridine, i.e., it should be free of reactive groups such as active hydrogen, and free of hydrolyzable groups such as esters, acyl halides, and the like. Suitable solvents include ketones, such as acetone or methyl ethyl ketone. Since the products of this invention are stable to acid or neutral hydrolysis, excess water may be used.

While preferred temperatures range from about 5° to 100° C., it will be appreciated that the exact reaction temperature used in any given situation is not critical. Thus, for example, lower temperatures may be used with longer reaction times.

The hydrolysis reaction can be conveniently monitored by examining the infrared spectra of the volatile materials since the fluoroaziridine products of this invention are solids or liquids of low vapor pressure at room temperature.

The fluoroaziridines of formula (2.2) are recovered by conventional techniques, such as vapor phase chromatography or distillation in the case of liquids, or recrystallization or sublimation in the case of solids.

The preferred compounds of formula (2.2) prepared by hydrolysis of compounds of formula (2.1) with water are shown in the following Table II.

TABLE II

| Fluoroaziridine of Formula (2.1) | Fluoroaziridine of Formula (2.2) |
|---|---|
| CF₂=N—N⌐CF₂CF₂⌐ | (⌐CF₂CF₂NNH⌐)₂C=O + |
|  | ⌐CF₂CF₂N—NH₂⌐ + ⌐CF₂CF₂N—N=C=O⌐ |
| CF₂=N—⌐NCF₂CFOCH₃⌐ | (CH₃OCFCF₂N—⌐NH⌐)₂C=O |
| CFBr=N—⌐N—CFBrCFC₅F₁₁⌐ | (C₅F₁₁CFCFBrN—⌐NH⌐)₂C=O + |
|  | ⌐C₅F₁₁CFCFBrN—NH₂⌐ |
| C₈H₁₇OCF=N—⌐NCF₂CFOC₈H₁₇⌐ | C₈H₁₇OCNH—⌐NCF₂CFOC₈H₁₇⌐ (with O double bond) |

The compounds of formula (1.3) having two or more functional groups (e.g. polyfunctional compounds) are useful as cross-linking agents or comonomers. For example,

OCNCFCF₂N—NCF₂CFNCO can be used to cross-link and cure low molecular weight polyvinyl alcohol and polyethylene imine.

Some of the compounds of formula (1.3) having imino groups can be used in cloth treating. For example,

CF₂=N—NCF₂CFC₇F₁₅ imparts oil resistant properties to cotton by virtue of the reaction of the CF₂=N— moiety with the free-hydroxyl groups of the cotton.

The compounds of formula (1.3) can be used as photolytically stable carbene generators owing to their ability to undergo controlled reversed reactions at moderate temperature. Thus, controlled pyrolysis of

CF₂CF₂N—NCF₂CF₂ in the presence of chlorine affords high yields of CF₂Cl₂, a known and useful refrigerant.

EXAMPLES

The following examples will more particularly illustrate the products and processes of the invention:

Example 1

Pyrolysis of Difluorodiazirine

A 26.0 g. (0.333 mole) sample of difluorodiazirine is pressurized into a 500 cc. autoclave formed of corrosion resistant, high nickel-copper iron alloy and is heated to 125° C. for 30 hours. After the pyrolysis period the volatile contents of the autoclave are transferred into a vacuum system and are separated by fractional distillation-condensation employing traps cooled to −78° and −196° C. Final purification is accomplished by vapor phase chromatography.

Perfluorocyclopropane (12.6 g., 75%) and CF₂=N—N=CF₂ (4.5 g., 21%) are the major products of the reaction and their presence is confirmed by spectral comparisons with authentic samples. The fluoroaziridine,

CF₂=N—NCF₂CF₂

(0.7 g., 4%), exhibits absorptions in the infrared spectrum at 5.68μ and 6.60μ due to the >C=N— and fluoroaziridine ring, respectively. The F¹⁹ n.m.r. spectrum shows a somewhat broadened absorption at 126.3 φ* (ring CF₂) and a typical CF₂=N— AB pattern at 49.4 and 75.7 φ* (JAB=65.2 cps). The mass spectrum is consistent for the structure assigned and shows a parent peak 178 (6%) C₃F₆N₂.

Elemental analysis indicates the fluoroaziridine to contain 63.2 percent fluorine and 16.0 percent nitrogen; theoretical is 64.0% of fluorine and 15.7% nitrogen.

The bis(fluoroaziridine),

CF₂CF₂N—NCF₂CF₂, is obtained in 0.01% yield (0.02 g.) and is identified on the basis of spectral considerations and molecular weight. In the infrared spectrum of the bis(fluoroaziridine) the principle absorption is due to the three-membered ring and appears at 6.63μ. The F¹⁹ n.m.r. spectrum is characterized by a single peak at 125.4 φ* and the molecular weight by effusion in the mass spectrometer is 221±5 (theory =228). The mass spectrum is consistent with the assigned structure.

Example 2
Pyrolysis of Difluoraminofluorodiazirine

A total quantity of difluoraminofluorodiazirine amounting to about 0.826 g. ($7.44 \times 10^{-3}$ mole), diluted with 0.291 g. ($2.4 \times 10^{-3}$ mole) of dichlorodifluoromethane, is condensed into three 2-cc. glass ampoules each cooled to $-196°$ C. and fitted with polytetrafluoroethylene valves. The ampoules are allowed to warm slowly to room temperature and then are heated to and maintained at about 75°-80° C. for 24 hours to subject the contents to pyrolysis conditions. After such pyrolysis is complete, the contents of each ampoule is combined and separated by fractional distillation-condensation on a vacuum line employing a series of traps cooled, respectively, to $-78°$, $-111°$, $-145°$, and $-196°$ C. The reaction mixture thus separated according to volatility, is found to have the following product distribution (in molar percent yield): $-78°$ (17-19%), $-111°$ (19-21%), $-145°$ ($CF_2Cl_2$), and $-196°$ C. (41-47%). The molar percent yields are based on complete thermal decomposition of difluoraminofluorodiazirine and on the following stoichiometry for each fraction: $-196°$ C., monomer products; $-111°$ C., dimer products, and $-78°$ C., a 1:1 mixture of dimer and trimer products.

Final purification is accomplished by vapor phase chromatography. The reaction mixture is thus found to contain $CF_2=NF$ (Ca. 45%), $NF_2CF_2CF=NF$ (Ca. 15%), $NF_2CF_2N=NCF=NF$, and $NF_2CF=N-N=CFNF_2$ (Ca. 10%), and

NF₂CF=N—NCF(NF₂)CF(NF₂)

(Ca. 2%).

The identity of

NF₂CF=N—NCF(NF₂)CF(NF₂)

is established by spectral considerations. The infrared spectrum shows the presence of the $>C=N-$ groups at $5.82\mu$ and the fluoroaziridine ring at $6.90\mu$. The molecular weight is shown to be 275 (theoretical is 277) by effusion rate in a mass spectrometer. The mass spectrum is consistent with the fluoroaziridine structure.

Example 3
Photolysis of Difluorodiazirine with $CF_2=N-N=CF_2$

A mixture of perfluoro-2,3-diazabuta-1,3-diene (10 equivalents) and difluorodiazirine (1 equivalent) is heated to 100° C. in a 200-cc. glass ampoule and irradiated with ultraviolet light of 3000-4000 Å. After completion of the photolysis period, the reaction mixture is found to contain a low yield (i.e., less than about 20%) of

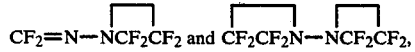
CF₂=N—NCF₂CF₂ and CF₂CF₂N—NCF₂CF₂, as well as $C_2F_4$ and

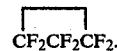
CF₂CF₂CF₂.

Example 4
Hydrolysis of

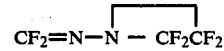
CF₂=N—N — CF₂CF₂

A sample of

CF₂=N—NCF₂CF₂ is condensed in vacuo at 196° C. into a glass hydrolysis bulb of 50-cc. capacity, containing a 1:8 mixture of water and acetone. The reactor is sealed, warmed to room temperature, and maintained at room temperature for one hour. All volatile products are then pumped off and the white solid residue is extracted with acetone. After filtration, the extract is evaporated to dryness and the residue sublimed in vacuo at 100° C. A 40% yield of

(CF₂CF₂NNH)₂C=O is obtained.

Absorptions appear at 3.08 (NH), 5.90 (C=O), 6.33 (NH), and 6.60 (fluoroaziridine ring) microns in its infrared spectrum. The $F^{19}$ nuclear magnetic resonance spectrum shows a single peak at 125.0 $\phi^*$. Elemental analyses result in 20.7% carbon and 18.7% nitrogen versus theoretical of 21.0% carbon and 19.6% nitrogen.

Infrared and mass spectral analysis shows that the volatile product mixture of the above reaction contains

CF₂CF₂N—NH₂ and CF₂CF₂N—N=C=O.

Example 5
Pyrolysis of Fluoromethoxydiazirine with $C_5F_{11}CF=N-N=CFC_5F_{11}$ A mixture of $C_5F_{11}CF=N-N=CFC_5F_{11}$ (10 molar equivalents) and fluoromethoxydiazirine (1 molar equivalent) is sealed in a glass ampoule and pyrolyzed at 100° C. for 24 hours. Fractional distillation-condensation of the reaction mixture followed by distillation affords a low yield of

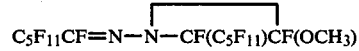
C₅F₁₁CF=N—N—CF(C₅F₁₁)CF(OCH₃)

which is identified by spectroscopic techniques.

Example 6

Hydrolysis of

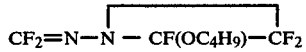

Using the procedure of Example 4,

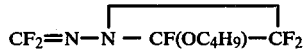

is hydrolyzed with a mixture of water and acetone. The purified solid product,

is obtained by recrystallization, and is identified by spectroscopic techniques.

Example 7

Pyrolysis of Cyanofluorodiazirine and CFBr=N—N=CFBr

Using the procedure of Example 5, CFBr=N—N=CFBr (1 molar equivalent) and cyanofluorodiazirine (1 molar equivalent) are pyrolyzed in a glass ampoule at 75° C. Fractional distillation-condensation followed by vapor phase chromatography affords low yields of CFBrCF(CN)N—NCF(CN)CFBr and

Both volatile products are identified by spectroscopic means.

Example 8

Hydrolysis of

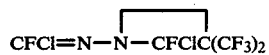

Using the procedure of Example 4,

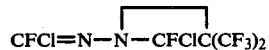

is hydrolyzed with a water-acetone mixture and affords a low yield of

Example 9

Pyrolysis of Bis(trifluoromethyl)diazomethane with $(CF_3)_2C=N—N=C(CF_3)_2$

Using the procedure of Example 5, a mixture of $(CF_3)_2C=N—N=C(CF_3)_2$ (1 molar equivalent) and bis(trifluoromethyl)diazomethane (1 molar equivalent) are pyrolyzed in a glass ampoule. Fractional distillation-condensation is followed by distillation and affords

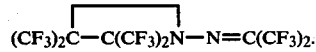

Identification is by infrared and nuclear magnetic resonance spectroscopy.

I claim:
1. A compound having the formula

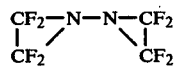

* * * * *